United States Patent [19]
Watkins et al.

[11] Patent Number: 6,159,473
[45] Date of Patent: *Dec. 12, 2000

[54] SORE THROAT SPRAY

[75] Inventors: Mary Beth Watkins, Bellingham; James H. Coyne, Blaine, both of Wash.

[73] Assignee: Botanical Laboratories, Inc., Ferndale, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 09/103,965

[22] Filed: Jun. 24, 1998

[51] Int. Cl.$^7$ .................................................. A61K 35/78
[52] U.S. Cl. ......................... 424/195.1; 424/45; 424/601
[58] Field of Search ................... 424/195.1, 45, 424/601; 514/849, 877

[56] References Cited

U.S. PATENT DOCUMENTS

| | | | |
|---|---|---|---|
| 4,154,823 | 5/1979 | Schutt | 424/195 |
| 5,100,898 | 3/1992 | Sorrentino | 514/281 |
| 5,296,225 | 3/1994 | Adekunle et al. | 424/195.1 |
| 5,762,963 | 6/1998 | Byas-Smith | 424/472 |
| 5,770,207 | 6/1998 | Bewicke | 424/195.1 |
| 5,834,443 | 11/1998 | Masiello | 514/44 |
| 5,891,465 | 4/1999 | Keller et al. | 424/450 |

FOREIGN PATENT DOCUMENTS

| | | |
|---|---|---|
| 2457691 | 1/1981 | France . |
| 04030734 | 2/1992 | Japan . |
| 8259452 | 10/1996 | Japan . |
| 8900858 | 2/1989 | WIPO . |

OTHER PUBLICATIONS

Kinghorn et al. Human Mediciinal Agents from plants. ACS symposium series. 534. pp. 28–29. Apr. 5–10, 1992.

Gottlieb et al (Editor). New Choices in natural healing. pp. 508–510, 1995.

Ritchason. The little herb encyclopedia—third edition. pp. 80, 81, 172, 173, 183, 184, 230 and 231, 1995.

Julia Lawless, The illustrated encyclopedia of essential oils. the complete guide to the use of oils in aromatherapy and herbalism. Pub. Elemental Books Limited. p. 201, 1995.

ACS Symposium series. Human medicinal agents from plants. Ed. Kinghorn et al. pp. 28–29. San Francisco, CA. Apr. 5–10, 1992.

Quisumbing. Republic of Philippines, Dept. of agriculture and natural Resources. Technical Bulletin 16. Medicinal plants of the Philippines, 1951.

Ritchason. The little Herb encyclopedia. third edition. pp. 8080, 81, 172, 173, 183, 184, 230 and 231, 1995.

*Primary Examiner*—Thurman K. Page
*Assistant Examiner*—Lakshmi Channavajjala
*Attorney, Agent, or Firm*—Benman & Collins

[57] ABSTRACT

A novel throat spray composition is provided that is useful for topical application to sore throats. The throat spray composition contains Piper methysticum (Kava Kava) as its main active ingredient, and is a suitable alternative to phenol-based over-the-counter throat sprays. Piper methysticum is used for its little known or utilized analgesic property, which provides a soothing and numbing effect to the throat. Additional ingredients include Echinacea angustifolia, Eucalyptus globulus, Thymus vulgaris, Lycopodium clavatum, Phytolacca decandra, Capsicum annum, Mentha piperita, and Phosphorus, which, together with Piper methysticum, offer temporary relief of sore throat pain, irritation, difficulty swallowing, and symptoms of hoarseness or laryngitis.

2 Claims, No Drawings

SORE THROAT SPRAY

BACKGROUND OF THE INVENTION

1. Field of the Invention

The present invention relates generally to non-prescription, homeopathic remedies, and, more particularly, to a throat spray free of phenol for sore throats.

2. Description of Related Art

The over-the-counter (OTC) market has offered spray products for the treatment of sore throats for many years. The majority of these products utilize phenol as their active ingredient. Phenol is the simple alcohol derivative of benzene. Both of these chemicals are listed by the Environmental Protection Agency (EPA) as extremely carcinogenic.

A natural, non-carcinogenic throat spray that is an alternative to phenol is thus desired. Such a throat spray must work quickly and provide superior sore throat relief while at the same time have a taste that is acceptable to consumers. In addition to the technical difficulties in formulating such a product, it is important that the product meet the regulatory requirements of the Federal Drug Administration (FDA) and Homeopathic Pharmacopoeia of the United States (HPUS) as a homeopathic drug product.

SUMMARY OF THE INVENTION

In accordance with the present invention, a sore throat spray is provided that contains Piper methysticum (Kava Kava) as its main active ingredient, in place of phenol. Addition of Echinacea angustifolia, in combination with several other homeopathic ingredients, primarily plant extracts, serves to combine the little-known analgesic effects of Kava Kava with the immune and antiseptic effects of Echinacea, and addresses the concomitant symptoms and acute pathology associated with sore throats, including hoarseness, sinus congestion, post-nasal drip, and the condition of the lining of the throat.

The resulting formulation utilizes the little-known analgesic activities of Kava Kava to produce a soothing and numbing effect. The additional ingredients serve to enhance the effect of Kava Kava and provide further ameliorative effects. The natural homeopathic throat spray of the invention provides temporary relief of sore throat pain, irritation, difficulty in swallowing, and symptoms of hoarseness or laryngitis.

DESCRIPTION OF THE PREFERRED EMBODIMENTS

The sore throat spray of the present invention contains Piper methysticum (Kava Kava) as a main active ingredient in place of phenol. Preferably, Piper methysticum is combined with Echinacea angustifolia, as well as one or more other homeopathic ingredients, primarily plant extracts. The other ingredients are as follows: Eucalyptus globulus, Thymus vulgaris, Lycopodium clavatum, Phytolacca decandra, Capsicum annuum, Mentha piperita, and phosphorus, all in a base of purified water, USP-grade ethyl alcohol, natural sweeteners, and natural flavors.

The foregoing homeopathic ingredients are used at concentration levels which fall within lower potency ranges in combination with Kava Kava. The concentration levels range, in homeopathic terms, from Mother Tincture (1x) to 12x, which is generally considered to be the upper range of "low potencies". In standard terminology, these concentrations range from about 1 part per trillion (ppt) to 100 mg/ml. The homeopathic ingredients meet the HPUS specifications.

The individual potencies or concentrations selected for each ingredient are specific for the types of actions desired in each case.

Piper methysticum is used at low potency, specifically as an analgesic. This is a little known or utilized property of this ingredient and is considered to make this use unique.

Echinacea is utilized at low potency because in the Mother Tincture form, it has pronounced antiseptic and analgesic effects.

Eucalyptus is used at low potency to loosen phlegm.

Thymus vulgaris is used at the 1x level to soothe the lining of the throat and the enhance the flavor of the throat spray. There is also some indication that thymol present in this extract interacts with the nervous system as a mild analgesic similar to phenol.

Lycopodium and Phytolacca are used at the 3x potency to soothe the throat and to ensure adequate absorption for their systemic effects on the sinuses and tonsils.

Capsicum is used for its homeopathic indication in sore throats with characteristic burning pain and cannot be used at too low a potency or it will irritate the membranes of the throat.

Mentha piperita is used for its soothing effects and to enhance the flavor of the throat spray. The component menthol may have a mild effect similar to that of thymol.

Phosphorus is a homeopathic ingredient which is indicated strongly for hoarseness and sore throat and is used at the lower limit of its solubility.

The foregoing ingredients are preferably employed in the potencies listed in Table I, below, which also lists the source of the ingredients and the Materia Medica Indication for each ingredient.

TABLE I

Preferred Potencies of Ingredients, Sources of Ingredients, and Indication.

| Ingredient (Source) | Potency | Materia Medica Indication |
| --- | --- | --- |
| Piper Methysticum (Kava Kava - root) | 1X | Pain, restlessness, bronchitis, topical analgesic |
| Echinacea angustifolia (Cone Flower - plant) | 1X | Sore throat, swollen tonsils, post-nasal drip |
| Eucalyptus globulus (Blue Gum Tree - leaves) | 1X | Burning throat, sensation of phlegm in throat, enlarged tonsils |
| Thymus vulgaris (Garden Thyme - plant) | 1X | Sore throat, worse when swallowing, burning in pharynx, respiratory infections |
| Lycopodium clavatum (Club Moss - plant) | 3X | Dryness of throat, inflammation, pain and stitches when swallowing, better with warm drinks, tonsils swollen |
| Phytolacca decandra (Pokeweed - plant) | 3X | Throat feels rough, narrow, constricted, hot, pain when swallowing, tonsils swollen, mucus and post-nasal drip, mumps |
| Capsicum annum (Cayenne - fruit) | 6X | Throat feels hot, inflamed extending into ear with pain, dryness in throat, burning, constriction, worse between swallowing |
| Mentha piperita (Peppermint - plant) | 6X | Throat dry, sore, larynx and trachea painful, voice raspy |
| Phosphorus (Phosphorus - mineral) | 6X | Hoarseness, sore throat, raw tickling, painful throat |

The foregoing ingredients are provided in a base of purified water, USP ethyl alcohol, natural sweeteners, and natural flavors. Examples of natural sweeteners include, but are not limited to, fructose, sucrose, succinat, rice syrup, glucose, stevia, glycerin, honey, barley malt, etc. Examples of natural flavors include, but are not limited to, peppermint, spearmint, wintergreen, thyme, fennel, anise, etc.

Homeopathy holds within its Pharmacopoeia the potential for hundreds of different combinations for the treatment of sore throats; however, the unique use of Piper methysticum as an analgesic for the throat is considered a first and is essential to the actions of the throat spray of the present invention. When further coupled with Echinacea, which has well-established immune and antiseptic effects, this combination creates a unique approach to the natural throat spray of the invention. There are other throat sprays that contain Echinacea, but none of these utilize the analgesic effects of Piper methysticum. The remaining homeopathic ingredients were selected to address the concomitant symptoms and acute pathology associated with sore throats, including hoarseness, sinus congestion, post-nasal drip, and the condition of the lining of the throat.

A number of separate focus groups for evaluation of the throat spray formula of the present invention were held during the course of product development. The objectives of these focus group evaluations ranged from simple taste tests to more controlled product comparisons, and were conducted with groups of 8 to 12 individuals.

To evaluate both the delivery system and the efficacy or perceived strength of the product, the proposed formula was tested by individuals in a direct comparison with a phenol-based product, Chloroseptic, which was already in the market. Individuals were asked to compare the ease of use and the effectiveness of the delivery of the sprayers. They were also asked to compare the perceived strength of the two products by comparing the numbing or analgesic effect of both.

To evaluate efficacy further, individuals with colds and sore throats were asked to try the throat spray of the present invention and report its effectiveness. They were asked to complete a questionnaire which requested information on their previous use of throat sprays, severity of their current symptoms, and their reaction to the test spray.

To evaluate the taste of the throat spray of the present invention, a range of flavor samples were prepared and participants were asked to rate each, based on criteria such as perception of strength, palatability, and pleasantness. These responses were utilized in fine-tuning the final flavor characteristics of the preferred throat spray composition.

In an alternative embodiment, the foregoing formulation may be prepared as an herbal product, in which case, extracts (fluid, solid, or freeze-dried) or powders of the respective components may be used in the base.

Thus, there has been disclosed a throat spray for topical application containing Piper methysticum (Kava Kava) as its active ingredient, in combination with Echinacea angustifolia and other homeopathic ingredients. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A throat spray for topical application to a sore throat, said throat spray free of phenol and comprising *Piper methysticum, Echinacea angustifolia, Eucalyptus globulus Thymus vulgaris, Lycopodium clavatum, Phytolacca decandra, Capsicum annum, Mentha piperita*, and Phosphorus, wherein each listed ingredient is present in a homeopathic potency as follows:

| Ingredient | Potency |
| --- | --- |
| *Piper methysticum* | 1X |
| *Echinacea angustifolia* | 1X |
| *Eucalyptus globulus* | 1X |
| *Thymus vulgaris* | 1X |
| *Lycopodium clavatum* | 3X |
| *Phytolacca decandra* | 3X |
| *Capsicum annum* | 6X |
| *Mentha piperita* | 6X |
| Phosphorus | 6X. |

2. A method of providing temporary relief of at least one of sore throat pain, irritation, difficulty swallowing, and symptoms of hoarseness or laryngitis in a throat, said method comprising:

topically applying to said throat a composition free of phenol and containing *Piper methysticum, Echinacea angustifolia, Eucalyptus globulus, Thymus vulgaris, Lycopodium clavatum, Phytolacca decandra, Capsicum annum, Mentha piperita*, and Phosphorus, wherein each ingredient is present in a homeopathic potency as follows:

| Ingredient | Potency |
| --- | --- |
| *Piper methysticum* | 1X |
| *Echinacea angustifolia* | 1X |
| *Eucalyptus globulus* | 1X |
| *Thymus vulgaris* | 1X |
| *Lycopodium clavatum* | 3X |
| *Phytolacca decandra* | 3X |
| *Capsicum annum* | 6X |
| *Mentha piperita* | 6X |
| Phosphorus | 6X. |

* * * * *